(12) United States Patent
Noritomi et al.

(10) Patent No.: US 8,066,918 B2
(45) Date of Patent: Nov. 29, 2011

(54) APPARATUS FOR PRODUCING PARTICLES, EMULSIFIER HOLDING MEMBER, METHOD FOR PRODUCING PARTICLES, AND METHOD FOR PRODUCING MOLECULAR MEMBRANE

(75) Inventors: Yasuko Noritomi, Kawasaki (JP); Hidetaka Noritomi, Kawasaki (JP); Yuji Kubota, Yokohama (JP); Takahiro Suzuki, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1188 days.

(21) Appl. No.: 11/687,995

(22) Filed: Mar. 19, 2007

(65) Prior Publication Data

US 2007/0228588 A1    Oct. 4, 2007

(30) Foreign Application Priority Data

Mar. 30, 2006   (JP) ................. 2006-094353

(51) Int. Cl.
  *A61K 9/127* (2006.01)
  *B01J 13/04* (2006.01)
  *B28B 1/54* (2006.01)
(52) U.S. Cl. ............................. 264/4.1; 425/5
(58) Field of Classification Search .................. None
  See application file for complete search history.

(56) References Cited

U.S. PATENT DOCUMENTS

| | | | |
|---|---|---|---|
| 5,326,484 A * | 7/1994 | Nakashima et al. | 516/29 |
| 7,268,167 B2 * | 9/2007 | Higuchi et al. | 516/9 |
| 2006/0220269 A1 | 10/2006 | Noritomi et al. | |

FOREIGN PATENT DOCUMENTS

| | | |
|---|---|---|
| JP | 6-71150 | 3/1994 |
| JP | 6-246150 | 9/1994 |
| JP | 11-139961 | 5/1999 |
| JP | 2005-185972 | 7/2005 |
| JP | 2006-272196 | 10/2006 |

OTHER PUBLICATIONS

Kobayashi et al AIChE Jounal 2002, p. 1639.*
Sinil Kim, et al., "Preparation of Cell-Size Unilamellar Liposomes with High Captured Volume and Define Size Distribution", Bichimica et Biophysica Acta, vol. 646, 1981, pp. 1-9.
Sachio Matsumoto, et al., "Preparation of Lipid Vesicles on the Basis of a Technique for Providing W/O/W Emulsions", Journal of Colloid and Interface Science, vol. 62, No. 1, Oct. 15, 1977, pp. 149-157.
M. I. Angelova, et al., "Preparation of giant vesicles by external AC electric fields. Kinetics and applications", Progress in Colloid and Polymer Science, 89, 1992, pp. 127-131.

(Continued)

*Primary Examiner* — Anne Gussow
*Assistant Examiner* — Thurman Wheeler
(74) *Attorney, Agent, or Firm* — Oblon, Spivak, McClelland, Maier & Neustadt, L.L.P.

(57) ABSTRACT

The invention provides an apparatus for producing molecular membranes or particles, having a) a fluid supplying member configured to store a fluid, b) a plunger unit configured to extrude the fluid from the fluid supplying member, and c) an emulsifier holding member having at least two or more through-holes for holding an emulsifier, the through-holes allowing the fluid extruded from the fluid supplying member to pass therethrough, the emulsifier holding member being attachable to and detachable from the fluid supplying member.

6 Claims, 9 Drawing Sheets

OTHER PUBLICATIONS

Patricia Bucher, et al., "Giant Vesicles as Biochemical Compartments: The Use of Microinjection Techniques", American Chemical Society, Langmuir, vol. 14, No. 10, 1998, pp. 2712-2721.

Office Action issued Aug. 24, 2010, in Japanese Patent Application No. 2006-094353.

Office Action issued Aug. 24, 2010, in Japanese Patent Application No. 2006-094353.

* cited by examiner

APPARATUS FOR PRODUCING PARTICLES, EMULSIFIER HOLDING MEMBER, METHOD FOR PRODUCING PARTICLES, AND METHOD FOR PRODUCING MOLECULAR MEMBRANE

CROSS-REFERENCE TO RELATED APPLICATIONS

This application is based upon and claims the benefit of priority from prior Japanese Patent Application No. 2006-094353, filed Mar. 30, 2006, the entire contents of which are incorporated herein by reference.

BACKGROUND OF THE INVENTION

1. Field of the Invention

The invention relates to an apparatus and method for producing particles. The invention also relates to an apparatus and method for producing a molecular membrane.

2. Description of the Related Art

Vesicles, one kind of particles, have characteristics such as cell-like function as well as sequestration, preservation, concealment, and sustained release of substances, and have been widely used in technical fields such as biological fields, pharmaceutics (DDS, gene-introduction vectors, artificial erythrocyte), food, cosmetics, painting materials, environments, biosensors, and bioreactors. There are innumerable kinds of vesicles. Vesicles produced using 50% or more of a lipid as an emulsifier are classified in liposome. Further, being obtained by suspending an emulsifier or amphipatic molecules in a water-based medium, vesicles like a closed cytoplasmic membrane having a double structure observed in a biological membrane are classified in unilamellar vesicles (unilamellar vesicles or monolamellar vesicles), and vesicles like a closed cytoplasmic membrane having no less than triple structure are classified in multilamellar vesicles. The aqueous phase in the multilamellar vesicles contain a single aqueous phase or a plurality of aqueous phase.

Further, depending on the particle sizes and structures, the vesicles are classified into large multilamellar vesicles (MLV), small unilamellar vesicles (SUV), large unilamellar vesicles (LUV), and giant vesicles. The MLV is produced by a thin film formation method; the SUV is produced by an ultrasonic method and surfactant treatment method; the LUV is produced by a reverse-phase evaporation method, a solvent injection method, a French press method, a coacervation method, or a microcapsule method (S. Matsumoto, M. Kohda, and S. Murata, J. Coll. Interface Sci., 62: 147 [1977]; and S. Kim and G. M. Martin, Biocihmica et Biophysia Acta, 646: 1 [1981]); and the giant vesicle is produced by an electro-formation method (M. I. Angelova, S. Soleau, Ph. Meleard, J. F. Faucon, and P. Bothorel, Progr Colloid Polym Sci., 89: 127 [1992]; and P. Bucher, A. Fischer, P. L. Luisi, T. Oberholzer, and P. Walde, Langmuir, 14, 2712 [1998]). The particle sizes of the MLV, SUV, LUV, and giant vesicles produced by the above-mentioned methods are in ranges of 0.4 to 3.5 µm, 0.025 to 0.05 µm, 0.03 to 9 µm, and 50 to 100 µm, respectively.

To produce vesicles exhibiting little inconsistency in particle size by the above methods for producing vesicles, a series of complicated states such as drying and stirring lipid, voltage application, evaporation, ultrasonic wave, pressing, centrifugation, gel filtration separation, and dialysis are required, and it takes a long time (from several hours to a week or more) for the production. In addition, to enclose a substance in the produced vesicles, sealing steps by an electric shock method, an injection method by micro-capillary, an electropolation method, or a calcium fusion method, and thus, the steps are considerably complicated. Further, in the above-mentioned sealing steps, the sealing efficiency of a substance in vesicles is very low. Furthermore, since the production conditions are very severe, it is impossible to directly seal a physiologically active substance. Moreover, it is needed to remove the substance which is not enclosed. Additionally, since lipid is hydrolyzed by water in the case of the unilamellar vesicles formed in an aqueous solution, long term preservation of the unilamellar vesicles is impossible. Specifically, although it is generally possible to preserve the unilamellar vesicles for at longest 5 to 7 days in cool storage (4° C.), it is desirable to use them within 24 hours.

Comprehensively, it is difficult to produce vesicles enclosing a physiologically active substance by a conventional automatic method for producing vesicles having particle sizes of a narrow range. Furthermore, since the particle sizes of the produced vesicles are small, it is impossible to enclose a large quantity of polymers such as protein, DNA, or RNA in highly active state per unit volume of the vesicles.

Vesicles are required to be available promptly at a time of being needed in a needed amount. Further, in the case of using vesicles as a drug delivery system (DDS), it is needed to control the particle diameter and thickness of vesicles in terms of control of the administration dose of the drug, control of the sustained release of the drug, and control of the absorption of the drug, and it is desired to supply vesicles having excellent stability and high drug enclosing ratio. Further, a method of administration of the drug depends on the particle size of vesicles. Specifically, in general, vesicles having a diameter of 1 to 20 µm are administered by intravenous injection, vesicles having a diameter of 50 to 300 µm are administered by intra-arterial injection, and vesicles having a diameter of 300 µm or greater are administered by abdominal injection or oral administration. As a result, it is indispensable to control the particle sizes of vesicles. However, presently, no method for simply and quickly producing vesicles having uniform particle sizes, high physiological activity, and high substance enclosing ratio has been made available.

Further, a molecular membrane as one aspect of vesicles is very useful in fields such as a biosensor, a bioreactor, medical care, extraction, and environmental assessment. A technique of forming a molecular membrane in a micro-channel has been already proposed (JP-A 2005-185972 [KOKAI]). It is desired to provide a production kit for a molecular membrane, besides the molecular membrane formation method. Specifically, it has been desired to provide a detachable, disposable, and compact production kit for a molecular membrane, which is usable for in-situ analysis and simple analysis, that is, a molecular membrane production kit which can produce a molecular membrane having a three-dimensional structure exhibiting little inconsistency in size and shape.

BRIEF SUMMARY OF THE INVENTION

An apparatus for producing molecular membranes or particles according to the invention comprises:

a) a fluid supplying member configured to store a fluid;

b) a plunger unit configured to extrude the fluid from the fluid supplying member; and c) an emulsifier holding member having at least two or more through-holes for holding an emulsifier, the through-holes allowing the fluid extruded from the fluid supplying member to pass therethrough, the emulsifier holding member being attachable to and detachable from the fluid supplying member.

A method for producing particles according to the invention comprises:

a) holding an emulsifier in through-holes which allow a fluid extruded from a fluid supplying member to pass therethrough;

b) storing a fluid in the fluid supplying member; and c) extruding the fluid stored in the fluid supplying member via through-holes holding the emulsifier outside of the through-holes.

A method for producing a molecular membrane according to the invention comprises:

a) holding an emulsifier in through-holes which allow a fluid extruded from a fluid supplying member to pass therethrough;

b) storing a fluid in the fluid supplying member; and c) forming molecular membranes at the tip end parts of the through-holes by extruding the fluid stored in the fluid supplying member to the through-holes holding the emulsifier.

DETAILED DESCRIPTION OF THE INVENTION

Figure 1:
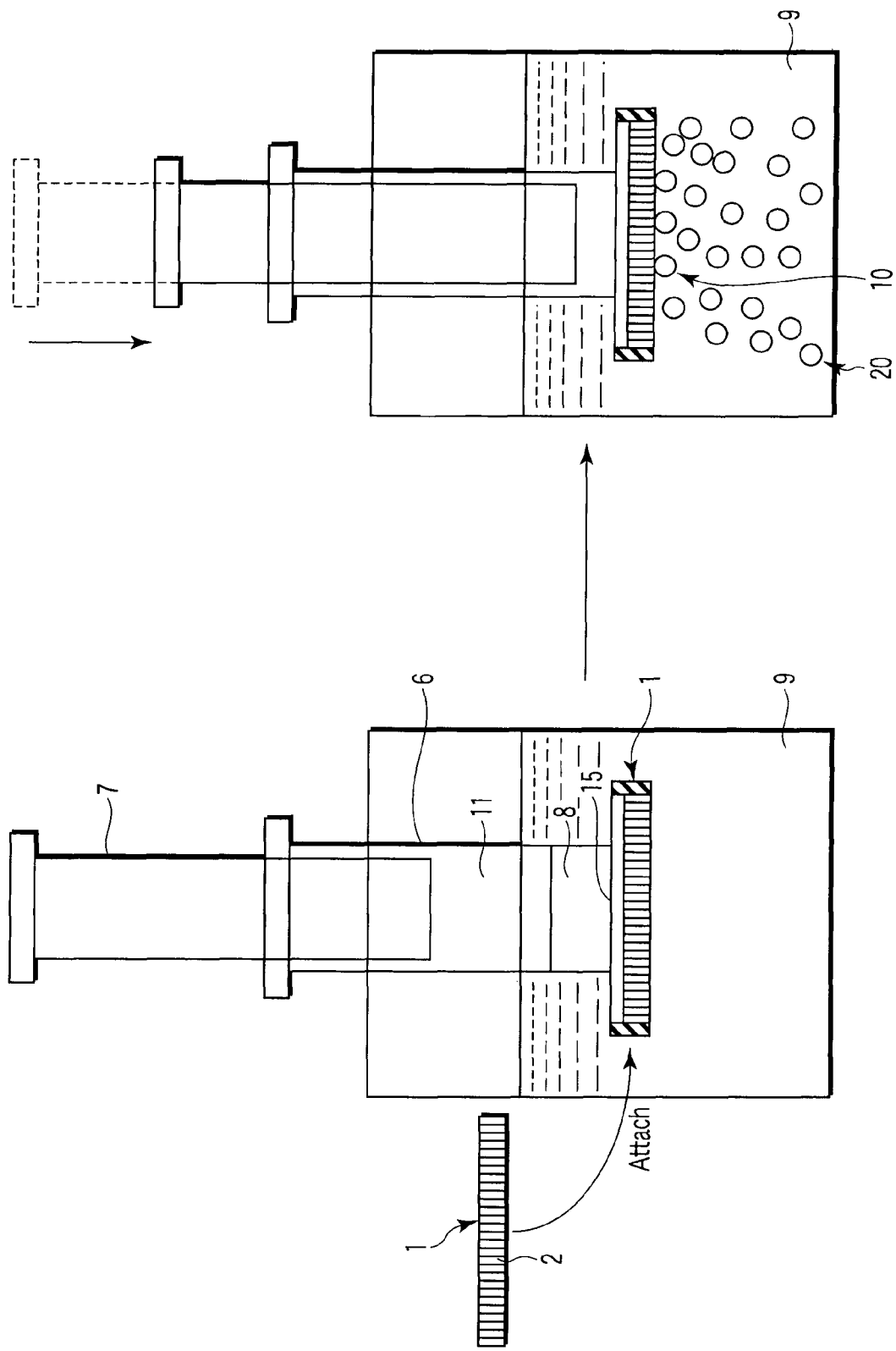
FIG. 1 is a schematic illustration 1 of an apparatus for producing particles according to a first embodiment.

Hereinafter, embodiments of the invention will be described in detail with reference to the drawings. Hereinafter, in the description of the drawings, the same or analogous reference numerals are assigned to the same or analogous parts. However, the drawings are schematic and it should be realized that the ratios of the respective sizes of the drawings are different from the actual ones. Accordingly, the specific sizes or the like should be determined along with the following descriptions. Further, respective size relations and ratios may be partially different among these drawings.

First Embodiment

A first embodiment is an apparatus and method for producing vesicles such as vesicles, unilamellar vesicles, multilamellar vesicles, liposome, reversed vesicles, reversed multilamellar vesicles, or bubbles, in which particles exhibiting little inconsistency in particle diameter, film thickness and enclosed capacity. Further, the first embodiment is suitable for enclosing a large quantity of a physiologically active substance such as a drug in vesicles and keeping the activity at a high level.

Basic Structure of Apparatus for Producing Vesicles

An apparatus for producing vesicles shown in FIG. 1 comprises a fluid supplying member 6 to which a first fluid 8 is stored, a plunger unit 7 for extruding the first fluid 8 from the fluid supplying member 6, and an emulsifier holding member 1 having through-holes 2 through which the first fluid 8 extruded from the fluid supplying member 6 passes. The emulsifier holding member 1 is attachable to and detachable from the fluid supplying member 6. The emulsifier holding member 1 is attached to the side of a lead-out port 15 of the fluid supplying member 6 by a fitting or pinching method. The emulsifier holding member 1 has at least two or more through-holes 2. Since the emulsifier holding member 1 has a plurality of through-holes, a large number of vesicles can be produced by one time operation of the plunger unit 7. Further, an emulsifier is held in the through-holes 2. The emulsifier holding member 1 having the emulsifier held in the through-holes 2 is attached to the fluid supplying member 6 to lead the first fluid 8 to the fluid supplying member 6. At that moment, the through-holes 2 are blocked with the emulsifier, and thus, the first fluid 8 remains in the fluid supplying member 6 without passing through the through-holes. At that time, when a pressure is applied to the first fluid 8 by operating the plunger unit 7, the first fluid 8 passes through the through-holes 2 together with the emulsifier and is pushed into a second fluid 9. As a result, vesicles enclosing the first fluid 8 covered with the emulsifier in the outside can be produced in the second fluid 9.

In the case a liquid is used as the first fluid 8, a third fluid 11 may be put in the fluid supplying member 6. The third fluid 11 is desirably a gas. The gaseous third fluid 11 is packed in the inside of the fluid supplying member 6 above the first fluid 8. The quantities of the first fluid and the third fluid are properly optimized. In the same manner as described above, the first fluid 8 and the third fluid 11 are pushed out to the second fluid 9 after having passed through the through-holes 2 by the plunger unit 7 and separated from the emulsifier holding member 1. Existence of the third fluid can decrease unintentional contamination of the second fluid 9 by the first fluid 8.

Figure 2:
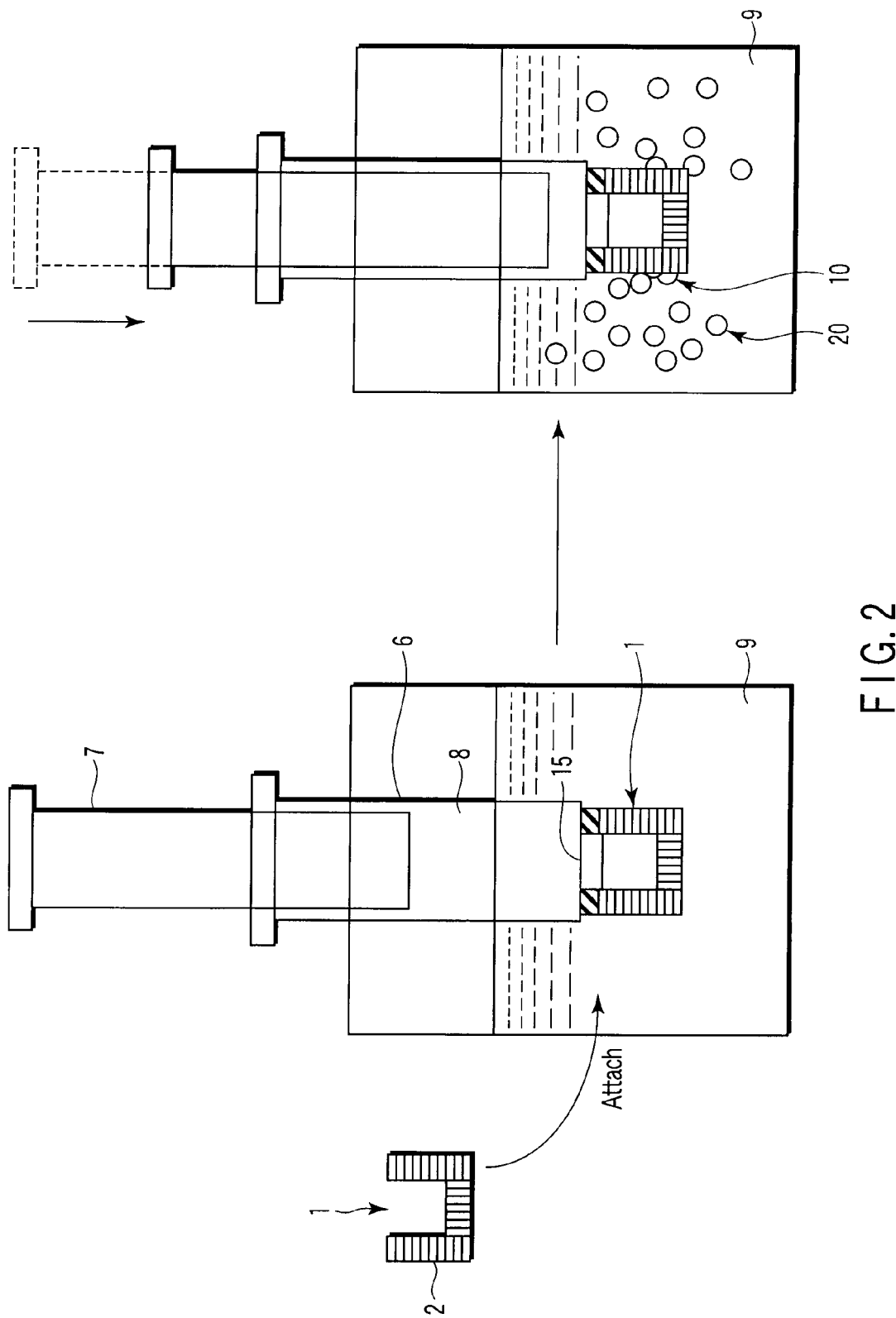
FIG. 2 is a schematic illustration 2 of an apparatus for producing particles according to the first embodiment.

The apparatus for producing vesicles shown in FIG. 2 is equipped with a cylindrical emulsifier holding member 1. The emulsifier holding member 1 is attachable to and detachable from the fluid supplying member 6, and has at least two or more through-holes 2 in a circular wall face. An emulsifier is held in the through-holes 2. The other configurations than that are same as those of the apparatus illustrated in FIG. 1.

Figure 3:
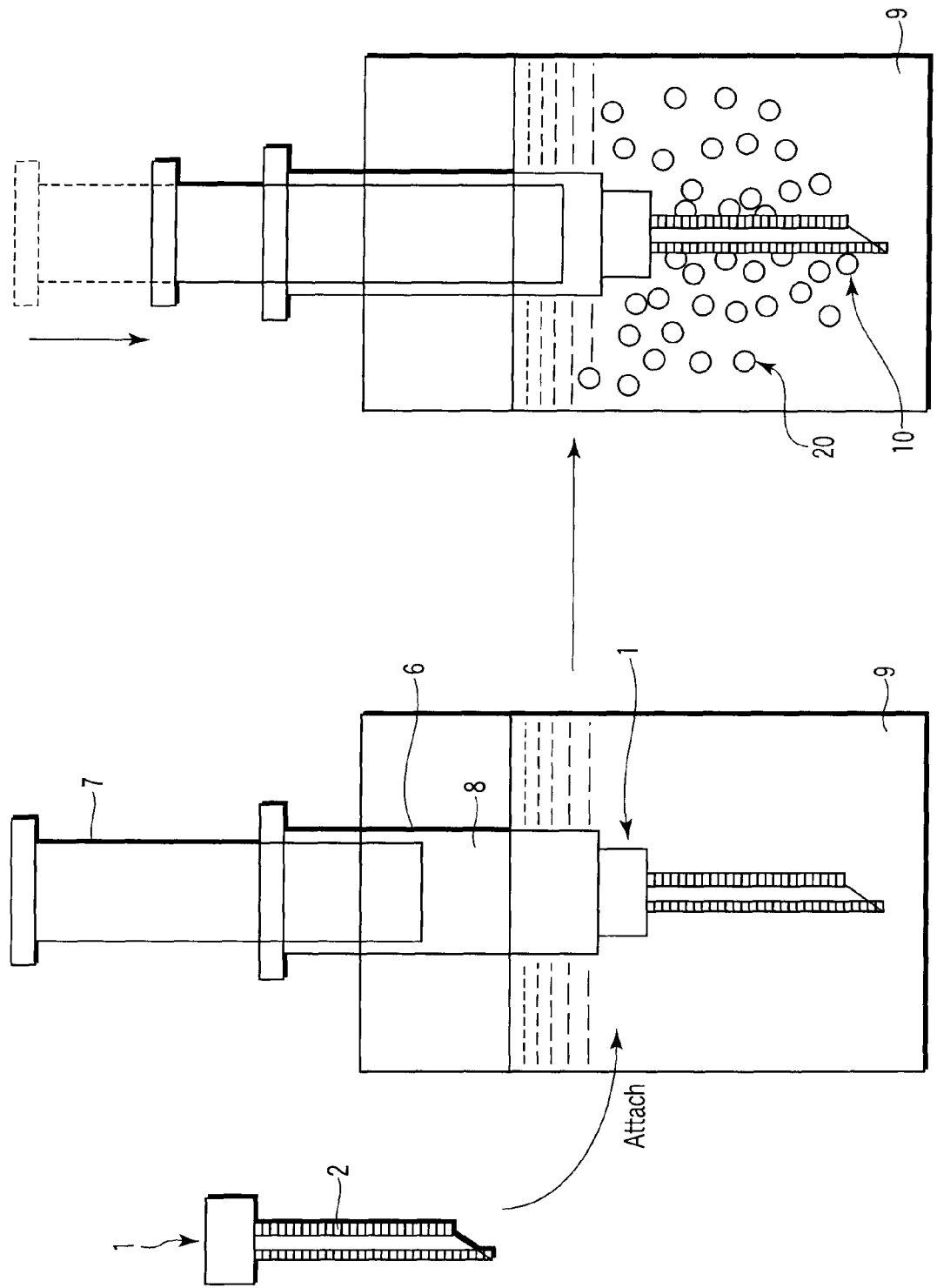
FIG. 3 is a schematic illustration 3 of an apparatus for producing particles according to the first embodiment.

The apparatus for producing vesicles shown in FIG. 3 is equipped with a needle-like emulsifier holding member 1. The emulsifier holding member 1 is attachable to and detachable from the fluid supplying member 6, and has at least two or more through-holes 2 in a needle-like wall face. An emulsifier is held in the through-holes 2. The other configurations than that are same as those of the apparatus illustrated in FIG. 1.

In addition, the emulsifier holding member 1 may be formed in a proper shape depending on the applications. For example, although the through-holes are formed in the side face in the needle-like emulsifier holding member shown in FIG. 3, the through-holes may be formed at the tip end. This embodiment will be described in detail with reference to FIG. 6. Further, the emulsifier holding member 1 may not be attachable to and detachable from the fluid supplying member 6 but the emulsifier holding member and the fluid supplying member may be integrated with each other. Furthermore, the fluid supplying member 6 and the plunger unit 7 are not particularly limited in the materials and shapes, and any kind of embodiments capable of achieving the above-mentioned objects may be included if it is within the scope of the invention.

Figure 4:
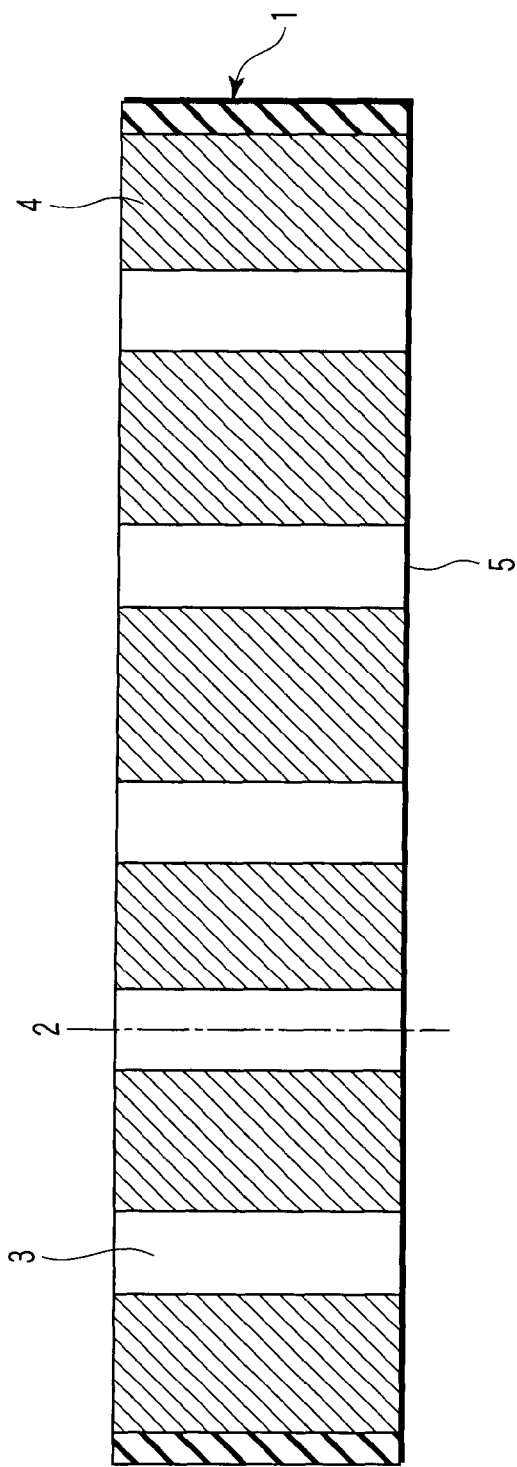
FIG. 4 is a structural illustration 1 of an emulsifier holding member.

The emulsifier holding member 1 illustrated in FIG. 4 has a film-like member 4 attachable to and detachable from the fluid supplying member 6, and at least two or more through-holes 2 are formed in the film-like member 4. The through-holes 2 are pores through which the first fluid 8 pushed out of the fluid supplying member 6 passes, and the through-holes 2 penetrate the film-like member from the fluid supplying member side to the lead-out port 5 side. Further, an emulsifier 3 is held in the through-holes 2. The emulsifier 3 may be held previously in the through-holes 2 or may be held separately at the time of use.

Figure 5:
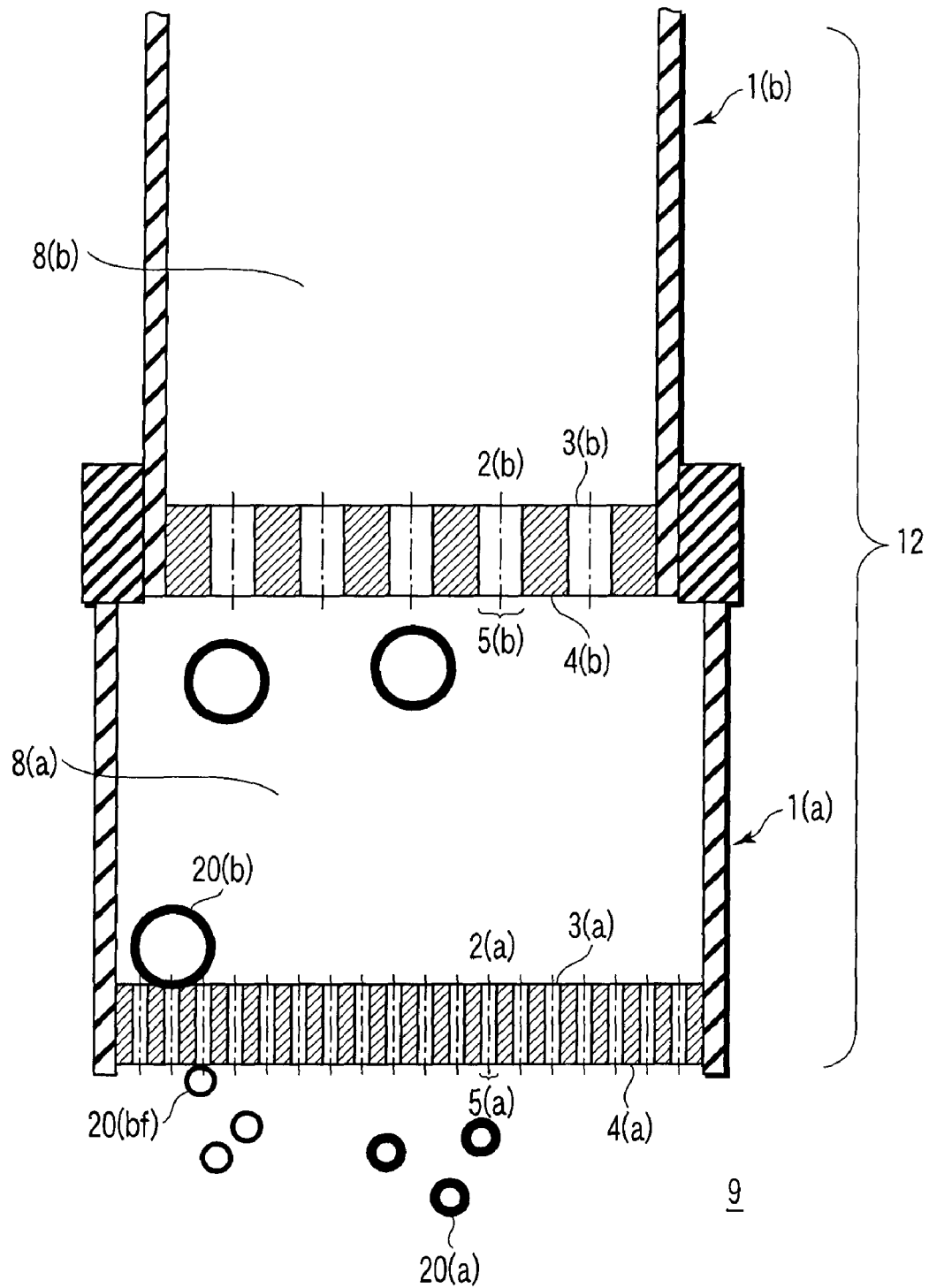
FIG. 5 is a structural illustration 2 of the emulsifier holding member.

FIG. 5 shows another embodiment of the emulsifier holding member 1. In this embodiment, the emulsifier holding member 1 includes two members, i.e., a member 1(a) and a member 1(b). Hereinafter, the emulsifier holding member 1 of this embodiment is denoted as emulsifier holding member 12.

The emulsifier holding member 12 can simultaneously produce vesicles of different sizes and/or thicknesses. Specifically, in FIG. 5, small multilamellar particles 20(a) of large thickness, large multilamellar particles 20(b) of large thickness, and small multilamellar particles 20(bf) of small thickness are produced. As described, vesicles of different sizes and/or thicknesses can be simultaneously produced by the emulsifier holding member 12, the sustained release speed of a drug can be controlled. That is, in the case where the vesicles produced in this manner are used as DDS, the term of curing efficacy can be properly controlled.

To simultaneously produce the vesicles of different sizes and/or thicknesses, the emulsifier holding member 12 comprises the following configuration.

The emulsifier holding member 12 comprises the members 1(a) and 1(b). A tip end of the member 1(b) is attached to the lead-out port 15 of the fluid supplying member 6. The inside of the member 1(b) is filled with a fluid 8(b). On the other hand, the member 1(a) is attached to a tip end of the member 1(b). A constant space is formed between the members 1(a) and 1(b), and the space is filled with the fluid 8(a). Next, a plurality of through-holes 2(a) and through-holes 2(b) are formed respectively in a film-like member 4(a) and a film-like member 4(b), and the through-holes 2(a) and 2(b) are respectively filled with emulsifiers 3(a) and 3(b). The diameter of the through-holes 2(a) is smaller than that of the through-holes 2(b).

The emulsifier holding member 12 having the above-mentioned configuration is attached to the fluid supplying member 6, and the plunger unit 7 is pushed in the inside of the fluid supplying member 6. Accordingly, the fluid 8(b) is pushed downward to produce particles 20(b) enclosing the fluid 8(b) with the emulsifier 3(b). Next, the fluid 8(a) is pushed downward to produce particles 20(a) enclosing the fluid 8(a) with the emulsifier 3(a). Finally, the particles 20(b) pass through the through-holes 2(a) to produce particles 20(bf).

Next, a method of assembling the emulsifier holding member 12 will be described.

There are following two methods for assembling the emulsifier holding member 12: (i) a method for first connecting the members 1(a) and 1(b), and then connecting the united members to the fluid supplying member 6 which is a main body; and (ii) a method for connecting the member 1(b) to the fluid supplying member 6 which is a main body, and successively connecting the member 1(a) to the tip end of the member 1(b).

(i) First, the emulsifier 3(a) and the fluid 8(a) are held in the member 1(a). Similarly, the emulsifier 3(b) and the fluid 8(b) are held in the member 1(b). Next, the member 1(a) and the member 1(b) are connected to each other to complete the emulsifier holding member 12. Finally, the emulsifier holding member 12 is connected to the fluid supplying member 6.

(ii) First, the emulsifier 3(a) and the fluid 8(a) are held in the member 1(a). Similarly, the emulsifier 3(b) and the fluid 8(b) are held in the member 1(b). Next, the member 1(b) is connected to the fluid supplying member 6. Finally, the member 1(a) is connected to the member 1(b).

Figure 6:
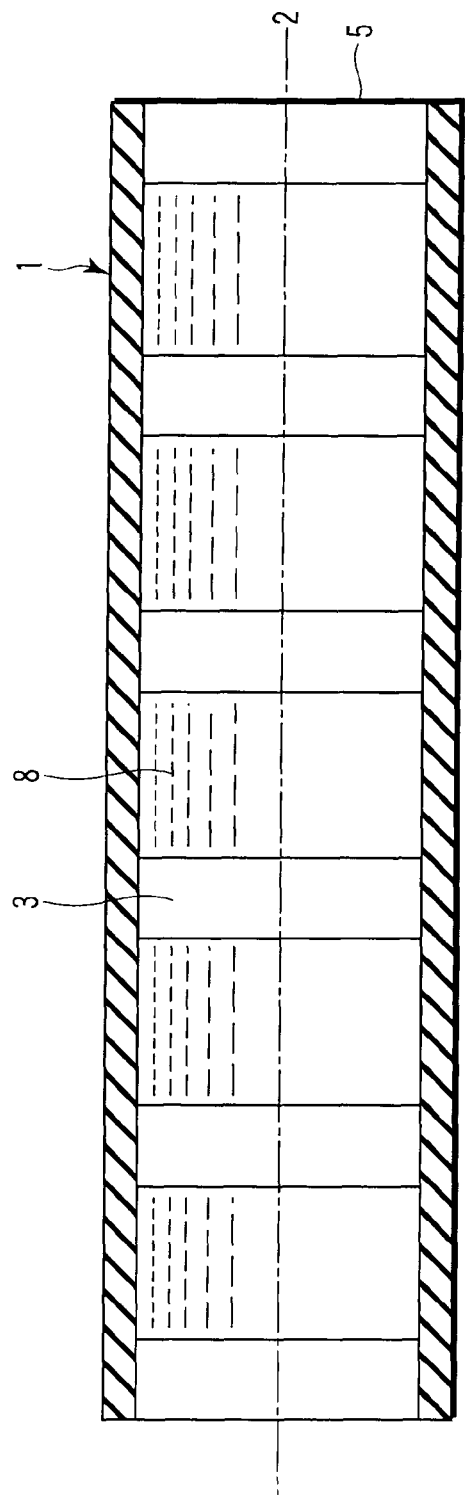
FIG. 6 is an enlarged view of a through-hole in which an emulsifier and a first fluid are reciprocally held.

FIG. 6 shows another embodiment, as a substituting embodiment, having a configuration of reciprocally holding the emulsifier 3 and the first fluid 8 in the through-holes 2 formed in the emulsifier holding member 1. A plurality of particles per through-hole can be produced by reciprocally holding the emulsifier 3 and the first fluid 8. In this case, air is in the fluid supplying member 6 and the air in the fluid supplying member is compressed by the plunger unit 7, so that the emulsifier 3 and the first fluid 8 held reciprocally in the insides of the through-holes 2 of the emulsifier holding member 1 are successively pushed out of the lead-out ports 5. Theoretically, the particles in numbers of repeat supply of the emulsifier 3 and the first fluid 8 are produced.

FIGS. 7 to 12 will be described later.

Subsequently, the film-like member 4 will be described in detail.

A nano-porous film may be used as the film-like member 4. Further, a metal film having fine pores, a synthetic resin film, or a film composed of a flexible metal layer and a resin layer formed on one face of the metal layer may be used. The resin sheet and the resin layer may be formed by using one or more kinds of resins and two or more kinds of resins, respectively. On the other hand, the metal layer may be formed by using one metal or two or more kinds of metals. The synthetic resin is not particularly limited, and may be selected from a group consisting of polyethylene resins, polypropylene resins, polystyrene resins, polyvinyl chloride resins, polyvinyl acetate resins, poly(methyl methacrylate) resins, rubber type resins, polyester resins, polyurethane resins, tar epoxy resins, epoxy resins, vinyl resins, acrylic resins, urea resins, aminoalkyd resins, alkyd resins, phenol resins, melamine resins, poly (vinylidene fluoride) (PVdF). The synthetic resin may be used in form of a non-woven fabric. Other than the above-mentioned examples, rubber materials having fine pores and Teflon (registered trademark) membranes may be also usable.

The nano-porous film produced from aluminum, titanium, silicon or the like may be controllable in not only the diameter (fine hole diameter) of the through-holes but also in the depth (thickness) of the through-holes (fine pores). In the case of using these materials, it is preferable that the surfaces of outer materials of the through-holes (fine pores) or the tip end wall faces of the through-holes (micropores) have high affinity with the emulsifier. The high affinity of the inside or the outside of the fine holes can be achieved by properly carrying out electroplating or electroless plating.

Further, a member having flexibility may be used as the emulsifier holding member 1 and may be deformed to widen the through-holes 2. For example, in the case where an elastic member or a deformable member is used for the emulsifier holding member 1, the through-holes 2 can be widened if the emulsifier holding member 1 is installed in the fluid supplying member 6. Also, the deformable emulsifier holding member 1 may be expanded after being installed in the fluid supplying member 6 to widen the through-holes 2.

Next, the emulsifier 3 will be described in detail.

The emulsifier 3 held in the through-holes 2 of the emulsifier holding member 1 may be one or more kinds of emulsifiers. The emulsifier 3 may be properly selected from lipids, boundary lipids, sphingolipids, fluorescent lipids, cationic surfactants, anionic surfactants, amphoteric surfactants, nonionic surfactants, synthetic polymers, and natural polymers such as proteins. As long as stable particles 20 are produced by using the emulsifier 3, the emulsifier 3 is not particularly limited in the type and the combination.

In the case of using a lipid as the emulsifier 3, the following lipid may be used without limitation: triolein, monoolein, egg yolk lecithin, phospholipids, synthetic lipids, lysophospholipids, glycosyldiacylglycerols, plasmalogens, sphingomyelins, gangliosides, fluorescent lipids, sphingolipids, sphingoglycolipids, lecithins, steroids, sterols, cholesterol, cholesterol oxide, dihydrocholesterol, glyceryl distearate, glyceryl monooleate, glyceryl dioleate, isosorbate monobrassidate, sorbitan tristearate, sorbitan monooleate, sorbitan monopalmitolate, sorbitan monolaurate, sorbitan monobrassidate, dodecylic acid phosphoate, dioctadecyl phosphate, tocopherol, chlorophyll, xanthophyll, phosphatidal ethanolamine, phosphatidal serine, inositol, hexadecyltrimethylammonium bromide, diglycosyl diglyceride, phosphatidyl choline, retinol/cholesterol oxide/lectin/rhodopsin, total brain lipids, human erythrocyte total lipids, and/or, natural lipids and synthetic lipids which can be produced as particles 20.

In the case of using a surfactant as the emulsifier 3, surfactants to be used are not particularly limited, and examples thereof include alkyl quaternary ammonium salts (e.g., CTAB, TOMAC, etc.), alkyl pyridinium salts (e.g., CPC), dialkylsulfosuccinic acid salts (e.g., AOT), dialkylphosphoric acid salts, alkylsulfuric acid salts (e.g., SDS), alkylsulfonic acid salts, polyoxyethylene type surfactants (Tween type, Brij type, Triton type, etc.), alkyl sorbitan (Span type), lecithin type surfactants, betaine type surfactants, and sucrose fatty acid esters.

In the case of using a polymer emulsifier as the emulsifier 3, it is not particularly limited, and examples to be usable as the emulsifier include polysoap, polyethylene glycol, polyvinyl alcohol, and polypropylene glycol.

In the case of using a protein emulsifier as the emulsifier 3, it is not particularly limited, and examples to be usable as the emulsifier may include casein.

The melting point, HLB value, viscosity, and specific gravity of the emulsifier 3 may be controlled by properly mixing emulsifies having different melting points, HLB values, viscosities, and specific gravities, or may be controlled by properly selecting the type of a solvent in which the emulsifier is dissolved or the ratio of the solvent. In terms of easy and quick production of the vesicles, it is preferable that solvent removal is no need after production of the particles. Accordingly, it is preferable to use no solvent or to suppress the use amount of the solvent to the minimum.

The emulsifier 3 may contain at least one or more kinds of other substances. Examples of the other substances may include proteins (e.g., enzymes, molecular chaperones, antigens, antibodies, hormones, etc.), nucleic acids, nucleic acid-relevant substances, photosensitive molecules, glycolipids, cholesterols, fluorochrome, ligands, photosensitive molecules, ion channels, electron conjugated substances, supporting surfactants, crown ethers, fullerenes, carbon nanotubes, carbon nanohorns, porphyrins, cyclodextrins, molecular tongues, particles, dendrimers, steroids, peptides, polypeptides, and saccharides. Addition of other substances to the emulsifier 3 makes it possible to produce particles modified with the various kinds of substances. As long as the produced particles can exist stably and above-mentioned other substances can exist stably in the inside of the molecular assembly of the emulsifier or the inner membrane or outer membrane of the vesicles or reversed vesicles, the types and combination of the emulsifier and other substances to be contained in the emulsifier are not particularly limited.

Next, the first fluid 8 will be described in detail.

The first fluid 8 is a fluid to be enclosed in the particles produced. The first fluid is a liquid, a liquid crystal, a gas, or their mixture. As a modified embodiment, for example, the emulsifier 3 and the first fluid 8 are reciprocally held in advance in the through-holes 2 of the emulsifier holding member 1 in the embodiment shown in FIG. 6. In this case, as long as the particles can exist stably, a liquid such as water or oil, and a liquid crystal; a gas; and their mixture may be properly selected to be used as the first fluid 8. In the case where air, for example, is used as the first fluid 8, air in the fluid supplying member is compressed by the plunger unit 7, and the emulsifier and first fluid 8 reciprocally held in the insides of the through-holes 2 of the emulsifier holding member 1 are extruded from the lead-out ports 5. Theoretically, the particles in numbers of repeat supply of the emulsifier 3 and the first fluid 8 are produced.

Moreover, other substances may be added to the first fluid 8. The substances to be added to the first fluid 8 may be, for example, fragrant substances, odorous substances, drugs, pharmaceutics, dyes, fluorescent agents, saccharides, reducing agents, oxidizing agents peptides, polypepitides, proteins, nucleic acid, nucleic acid-relevant substances, dendrimers, carbon nanohorns, particles, metal particles, micelles containing oil-soluble drugs, reverse micelles containing water-soluble drug and protein in water pool, microbes such as lactic acid bacteria and *E-coli*, and/or liquid crystals. The substances to be added to the first fluid 8 may be the above-mentioned "other substances" existing in the molecular membranes formed using the emulsifier 3.

Finally, the second fluid 9 will be described. The second fluid 9 to be used may be a liquid such as water and oil. To increase the stability of composite type particles 20, a surfactant, a polymer, a saccharide or the like may be properly added to the second fluid 9. The second fluid 9 may be also a gas, and for example, the produced particles may be directly released to air.

Method For Producing Particles

In the apparatus for producing particles illustrated in FIGS. 1 to 3, a method for producing vesicles according to the invention involves a step of holding the emulsifier 3 in the insides of the through-holes 2 through which the first fluid 8 extruded from the fluid supplying member 6 passes; a step of storing the first liquid 8 in the fluid supplying member 6, and a step of extruding the first fluid 8 stored in the fluid supplying member 6 to the second fluid 9 through the through-holes 2 in which the emulsifier 3 is held. In the case where the emulsifier holding member 1 is attachable and detachable, the through-holes 2 are filled and blocked with the emulsifier 3, and the emulsifier holding member 1 is to be attached to the fluid supplying member 6, and thereafter, the first fluid 8 is supplied to the fluid supplying member 6. At that moment, the through-holes 2 are blocked with the emulsifier. For this reason, the first fluid 8 stays in the fluid supplying member 6 without passing through the through-holes. When a pressure is applied to the first fluid 8 by operation of the plunger unit 7, the first fluid 8 passes through the through-holes 2 together with the emulsifier and is extruded to the second fluid 9. At that time, particles enclosing the first fluid 8 whose outside is coated with the emulsifier can be produced in the second fluid 9.

Further, in another embodiment shown in FIG. 6, in place of supply of the first fluid 8 to the fluid supplying member 6, the emulsifier 3 and the first fluid 8 are reciprocally held in the insides of the through-holes 2, and then, air in the fluid supplying member is compressed by pushing the plunger unit 7 into the fluid supplying member 6 to extrude the emulsifier 3 and the first fluid 8 reciprocally held in the insides of the through-holes to the second fluid. In this embodiment, a plurality of particles can be produced for every through hole.

Figure 7:
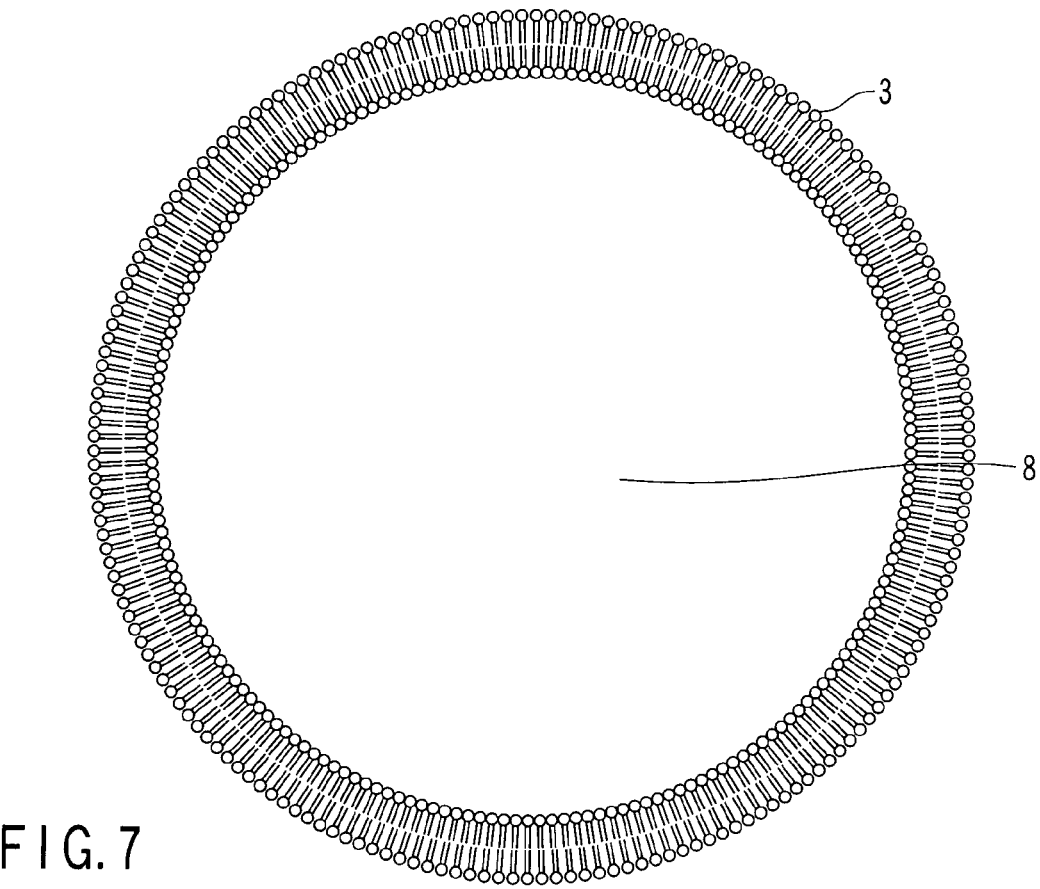
FIG. 7 is a schematic view of a unilamellar vesicle.
Figure 8:
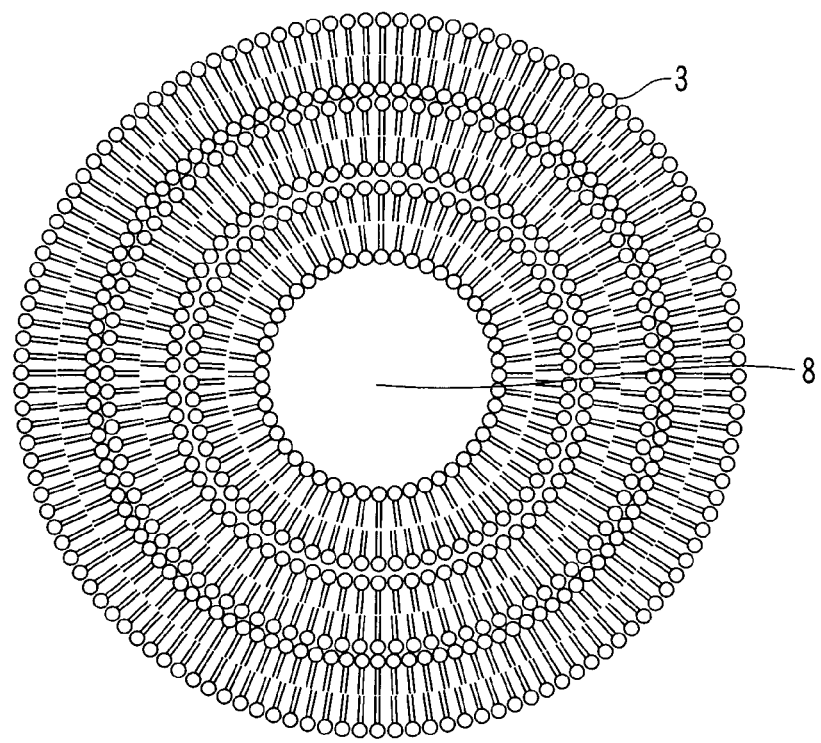
FIG. 8 is a schematic view of a multilamellar vesicle.

The particles produced may be vesicles, unilamellar vesicles, multilamellar vesicles, liposome, reversed vesicles, reversed multilamellar vesicles, or bubbles. FIG. 7 illustrates a schematic unilamellar vesicle and FIG. 8 illustrates a schematic multilamellar vesicle. The multilamellar vesicle of FIG. 8 has a multilayer structure of the emulsifier 3 and contains the first fluid 8 in the inside. It is made possible to produce vesicles having a desired number of layers by properly adjusting the amount of the emulsifier.

Next, the mechanism to produce a molecular membrane or a particle will be described with reference to FIGS. 9 and 10. The emulsifier 3 held in the inside of the through-holes 2 of the emulsifier holding member 1 is pushed toward the lead-out port 5 together with the fluid 8. The emulsifier remains for a while at the position while adhering to the lead-out port 5 due to the affinity. At that time, a semi-spherical molecular membrane 10 is formed between the first fluid 8 extruded from the through-hole 2 and the second fluid 9 in the outside of the system. The molecular membrane 10 has a semi-spherical form larger than the inner diameter of the lead-out port 5. When the first fluid 8 is further pushed outward the system, the semi-spherical molecular membrane is expanded and aged to be a microparticle, and the emulsifier is released from the lead-out port 5 while resisting against the affinity, thereby obtaining a particle 20 composed of the first fluid 8 enclosed in the emulsifier 3 in the second fluid 9.

Figure 9:
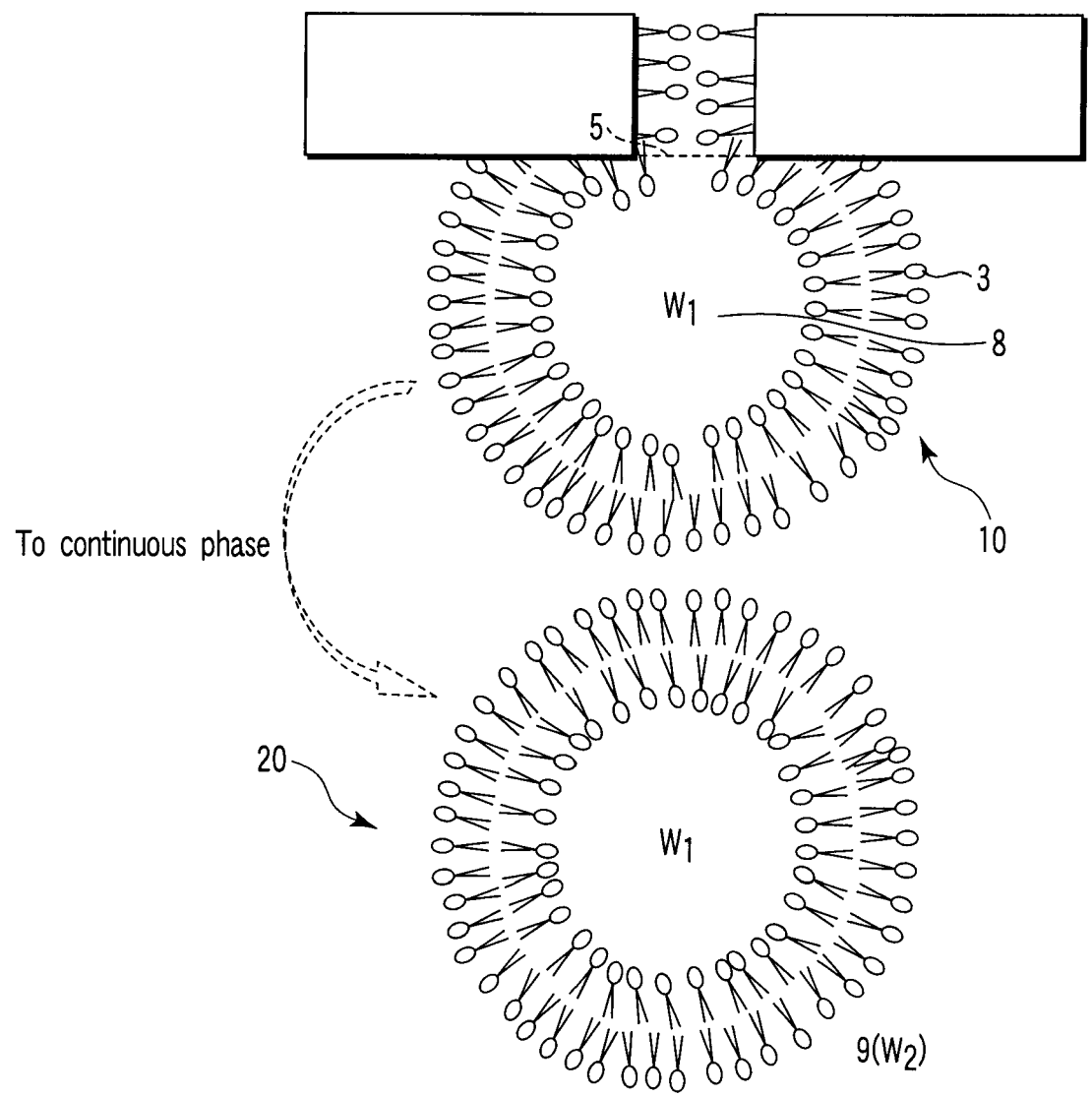
FIG. 9 is a schematic illustration showing a production mechanism for a $W_1/Os/W_2$ type molecular membrane and particles.

Herein, FIG. 9 is a schematic illustration showing mechanism to produce a $W_1/Os/W_2$ type molecular membrane or particle. The inner wall face of a through-hole (e.g., microchannels) of the emulsifier holding member 1 and the outer wall face of the lead-out port 15 are hydrophobic. A lipophilic emulsifier 3 (Os) is held in the through-hole 2, and a first fluid 8 ($W_1$) stored in the fluid supplying member 6 is extruded through the through-hole 2 holding the emulsifier 3 (Os) and pushed out of the lead-out port 5 to a second fluid 9 ($W_2$). Consequently, it is possible to produce a single inner aqueous phase type $W_1/Os/W_2$ emulsion composed of the first fluid 8 enclosed in the emulsifier 3, or a molecular membrane 10, or a particle 20 such as a vesicle, a unilamellar vesicle, a multilamellar vesicle or liposome. In this case, as shown in FIG. 9, the hydrophobic groups of the emulsifier 3 adhere to the outer wall face of the lead-out port 5 due to the hydrophobic interaction with the outer wall face of the hydrophobic lead-out port 5. Further, in an interface where the emulsifier 3 has contact with the first fluid 8 and an interface where the emulsifier 3 has contact with the second fluid 9, the hydrophilic groups of the emulsifier 3 are arranged in rows toward both sides of the first fluid 8 and the second fluid 9. A vesicle source is expanded into a semi-spherical or small spherical form with the emulsifier 3 as the boundary membrane (molecular membrane) along with the injection of the first fluid 8 into the inside of the emulsifier 3. Finally, when the semi-spherical or small spherical form becomes large in a release period, the vesicle source is separated from the outer wall face of the lead-out port 5 to be a single inner aqueous phase type $W_1/Os/$ $W_2$ emulsion, or a particle 20 such as a vesicle, a unilamellar vesicle, a multilamellar vesicle or liposome.

In the same principle, an lipophilic emulsifier 3 (Os) is held in the through-hole 2, and a first fluid 8 (V) stored in the fluid supplying member 6 is extruded through the through-hole 2 holding the emulsifier 3 (Os) and pushed out of the lead-out port 5 to a second fluid 9 ($W_2$) which is a water phase. As a consequence, it is possible to produce a molecular membrane, or a single inner vapor phase type $V/Os/W_2$ emulsion, or a particle 20 of a bubble. The hydrophobic groups of the emulsifier 3 adhere to the outer wall face of the lead-out port 5 due to the hydrophobic interaction with the outer wall face of the hydrophobic lead-out port 5. Note that, in the case of the single inner vapor phase type $V/Os/W_2$ emulsion, the hydrophobic groups and the hydrophilic groups of the emulsifier 3 are arranged in rows toward the first fluid 8 (V) and the second fluid 9 ($W_2$), respectively, in the first interface where the emulsifier 3 has contact with the first fluid 8 and the second interface where the emulsifier 3 has contact with the second fluid 9(not shown).

Figure 10:
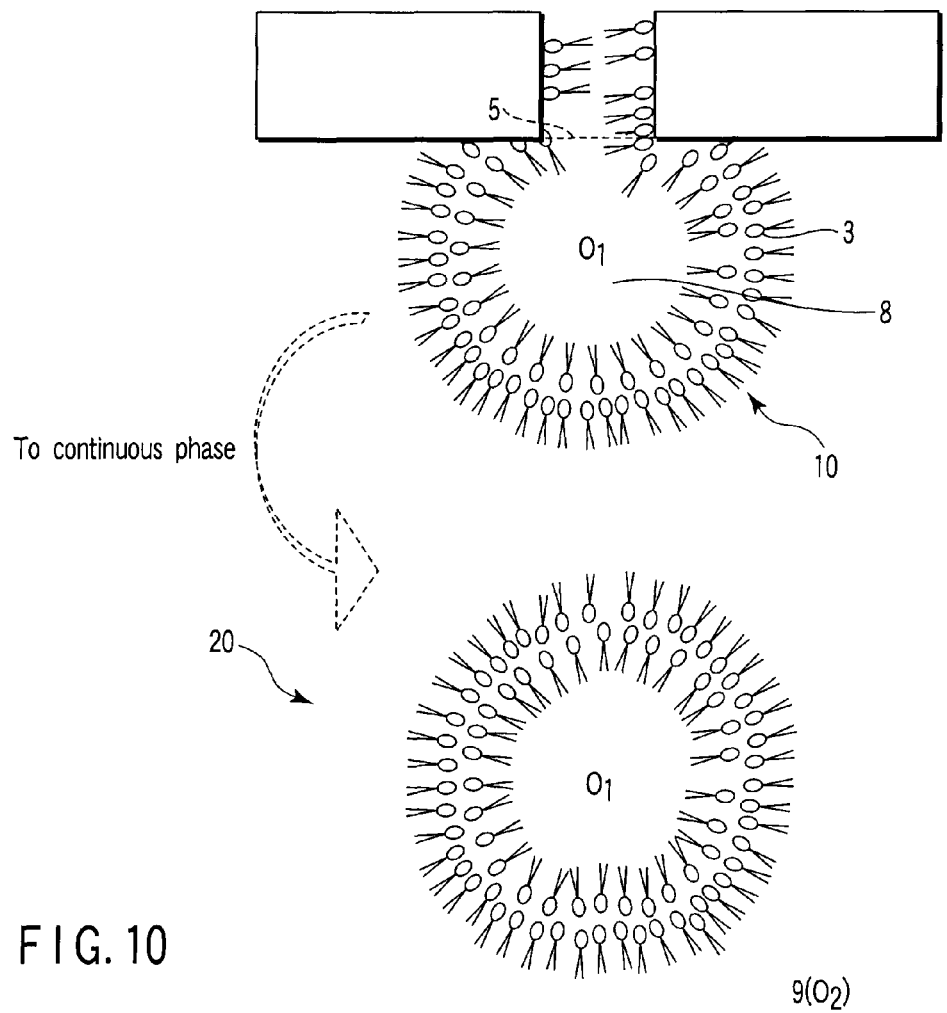
FIG. 10 is a schematic illustration showing a production mechanism for an $O_1/Ws/O_2$ type molecular membrane and particles.

FIG. 10 is a schematic illustration showing mechanism to produce a $O_1/Ws/O_2$ type molecular membrane or particle. The inner wall face of a through-hole is hydrophilic. A hydrophilic emulsifier 3 (Ws) is held in the through hole 2, and a first fluid 8 ($O_1$) stored in the fluid supplying member 6 is extruded through the through hole 2 holding the emulsifier 3 (Ws) and pushed out of the lead-out port 5 to a second fluid 9 ($O_2$) which is an oil phase. As a consequence, it is possible to produce a single inner oil phase type $O_1/Ws/O_2$ emulsion composed of the first fluid 8 enclosed in the emulsifier 3, or a reverse molecular membrane 10, or a particle 20 such as a unilamellar reverse vesicle or a multilamellar reverse vesicle. In this case, the emulsifier 3 adheres to the lead-out port 5 due to the hydrophilic interaction with the hydrophilic through hole 2. Further, in the interfaces where the emulsifier 3 has contact with the first fluid 8 and with the second fluid 9, the hydrophobic groups of the emulsifier 3 are arranged in rows toward both sides of the first fluid 8 and the second fluid 9. A vesicle source is expanded into a semi-spherical or small spherical form with the emulsifier 3 as the boundary membrane (molecular membrane) along with the injection of the first fluid 8 into the inside of the emulsifier 3. Finally, becoming large in a release period, the vesicle source is separated from the outer wall face of the lead-out port 5 to be a single inner oil phase type $O_1/Ws/O_2$ emulsion, or a particle 20 such as a reverse vesicle or a multilamellar reverse vesicle.

In the same principle, a hydrophilic emulsifier 3 (Ws) is held in the through-hole 2, and a first fluid 8 (V; vapor phase), stored in the fluid supplying member 6 is extruded through the through-hole 2 holding the emulsifier 3 (Ws) and pushed out of the lead-out port 5 to a second fluid 9 ($O_2$) which is an oil phase. As a result, it is possible to produce a molecular membrane, or a single inner vapor phase type $V/Ws/O_2$ emulsion or a bubble or a particular 20 of a single inner vapor phase type $V/Ws/O_2$ emulsion or a bubble (not shown).

A material which can attach the emulsifier 3 due to the affinity is used for the lead-out ports 5 of the through-holes 2. The surface property, particularly, the wettability, of the lead-out ports 5 of the through-holes 2 can be determined in relation to the emulsifier 3 and the first fluid 8. Note that, in place of the selection of the material of the lead-out ports 5, the surface property can be controlled by the surface treatment of the lead-out ports 5. For example, the wettability attaching the emulsifier 3 can be improved by surface roughening treatment of the lead-out ports 5.

Figure 11:
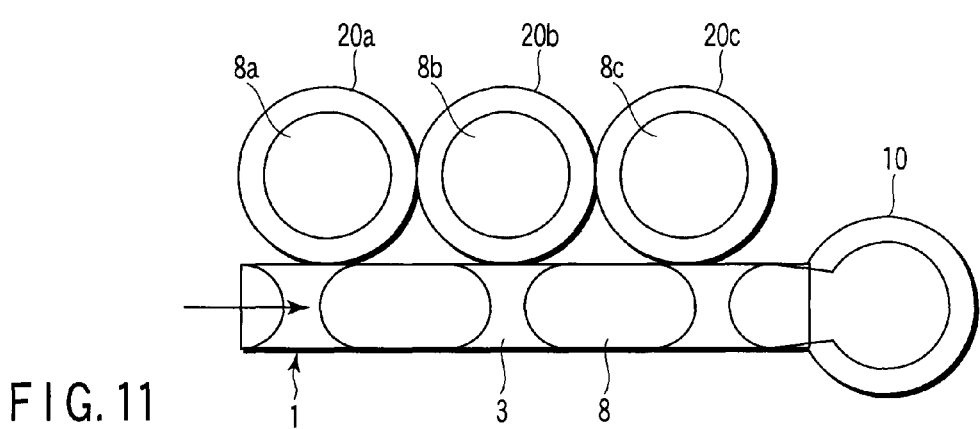
FIG. 11 is an enlarged view of a through-hole of an emulsifier holding member for producing particles having different compositions.

In the case where the emulsifier 3 and the first fluid 8 are reciprocally held in the through-holes 2 of the emulsifier holding member 1 as described in above-mentioned another embodiment of FIG. 6, various different kinds of substances may be added to the respective segments of the first fluid 8 to produce vesicles or reverse vesicles (particles 20a, 20b, and 20c) enclosing a different substance (8a, 8b, 8c) as illustrated in FIG. 11. Thus, vesicles or reverse vesicles modified with different substances in the inner membranes and the outer membranes can be produced.

In a method for producing the particles 20 according to the first embodiment, it is very important to control the temperature and the pressure. For example, Joule heat may be used for heating the system. Further, laser beam may be used for local heating. In the case of controlling the temperature of the production system, temperature control means is not particularly limited in the invention as long as the temperature of the emulsifier 3 and the first fluid 8 can be controlled directly or indirectly from the inside or the outside of the fluid supplying member 6 or the through-holes 2 or the temperature of the first fluid 8 is partially or entirely controlled.

When the particles 20 are to be produced in the apparatus for producing particles, the emulsifier 3 is supplied to the through-holes 2, and successively, the emulsifier holding member 1 is cooled to a melting point of the emulsifier 3 or lower. Thereafter, the emulsifier holding member 1 is heated to a melting point of the emulsifier 3 or higher before the emulsifier 3 and the first fluid 8 are extruded to the second fluid 9 to produce the particles 20.

An emulsifier alone may be used as the emulsifier 3 for producing the particles 20. Further, an emulsifier containing at least one kind of substance except water and an oil as the solvent of the emulsifier may be used. In this case, at the time of producing the particles 20, the emulsifier may be used while being kept at a temperature not lower than the melting point or the phase transfer temperature of the molecular membrane. At least one or more kinds of emulsifiers having different melting points may be used as the emulsifier 3. In the case where an emulsifier having a low melting point and an emulsifier having a high melting point are used in form of a mixture, the emulsifier having the higher melting point is used at a temperature lower than the melting point to produce the particles. For example, an emulsifier mixture obtained by mixing monoolein of a relatively high melting point with sorbitan monooleate of relatively low melting point(melting point 10 to 20° C.), has a melting point equal to or lower than the melting point (25° C. for $\alpha$-type and 35° C. for $\beta$-type) of monoolein, and the particles can be produced at the melting point of the emulsifier mixture or higher and the melting point of the monoolein or lower.

On the other hand, in the case of using an emulsifier having a high melting point, the emulsifier is held in the holding part 1 at a temperature lower than the melting point. Then, immediately before the use, the temperature is increased to the melting point or higher to produce the particles 20. Accordingly, in the holding part 1, phospholipids and emulsifiers having double bonds instable in ambient environmental conditions such as light and heat may be preserved for a long duration in the above-mentioned manner.

Further, the invention is suitable for producing particles by using the emulsifier 3 without using a solvent, particularly, a non-aqueous solvent, for dissolving the emulsifier. In this case, if an emulsifier or an emulsifier mixture having a predetermined HLB value based on the affinity of the emulsifier and the holding part is properly selected and employed, the particles may be produced without using any solvent for dissolving the emulsifier.

In general, an emulsifier having a low HLB value has high affinity with oil and exhibits lipophilicity. On the other hand, an emulsifier having a high HLB value exhibits hydrophilicity. Accordingly, as described above, the particles can be produced in such a manner that proper emulsifiers having different HLB values are mixed and an emulsifier mixture having HLB values in a wide range is used. For example, a series of sorbitan fatty acid esters having low HLB values (hereinafter, abbreviated as sorbitan ester) and a series of Tweens having high HLB values may be mixed properly to produce emulsifier mixtures having HLB values in a range of 4 to 17. Sorbitan monolaurate may be mixed with polyoxyethylene sorbitan monolaurate at a proper ratio to obtain emulsifier mixtures having HLB values in a range of 9 to 17. In addition, sorbitan monostearate may be mixed with polyoxyethylene sorbitan monostearate, or sorbitan monooleate may be mixed with polyoxyethylene sorbitan monooleate at a proper ratio to obtain emulsifier mixtures having HLB values in a range of 5 to 15. Further, also with respect to a series of sucrose fatty acid esters, those having different HLB values may be mixed at proper mixing ratios to obtain sucrose fatty acid ester type emulsifier mixtures having HLB values in a range of 1 to 19.

As described above, in the invention, the HLB value of an emulsifier mixture should be considered on the basis of the affinity of the emulsifier mixture 3 and the lead-out ports 15 of the emulsifier holding member. In the case where the emulsifier mixture remains at the lead-out ports 15 due to the affinity, the emulsifier mixture is extruded to the second fluid 9 while the first fluid 8 is injected to the emulsifier mixture, whereby a molecular membrane 10 can be produced. An emulsifier mixture having a proper HLB value may be used for producing the particles 20 composed of the first fluid 8 enclosed in the inside of the emulsifier mixture from the produced molecular membrane 10.

If particles are produced by using the emulsifier 3 containing no solvent for dissolving the emulsifier itself or the emulsifier 3 containing various kinds of substances, thermodynamically stable liposome, unilamellar vesicles, multilamellar vesicles, multilamellar reverse vesicles, or reverse vesicles can be produced.

In an embodiment of the invention, in the case of using the emulsifier 3 containing a solvent for dissolving the emulsifier itself, a double emulsion which is one kind of particles 20 is first produced. The emulsion is thermodynamically instable, and creaming, flocculation, Ostwald ripening, or coalescence may be caused with the lapse of time to result in phase separation of the oil phase and water phase. However, a step of heating, heating under diminished pressure, and/or bubbling an inert gas (argon gas, nitrogen gas, or the like) is carried out immediately after production of the double emulsion to remove the solvent for dissolving the emulsifier from the particles. As a consequence, liposome, unilamellar vesicles, multilamellar vesicles, multilamellar reverse vesicles, or reverse vesicles can be produced. In this case, it is not desirable from the viewpoint of quick production of the particles. However, if it is no need to consider the effect of the speed of the production or the effect of the solvent, liposome, unilamellar vesicles, multilamellar vesicles, multilamellar reverse vesicles, or reverse vesicles may be produced by carrying out the above-mentioned step of heating, heating under diminished pressure, and/or bubbling an inert gas (argon gas, nitrogen gas, or the like).

Applied Example

In the above-mentioned production apparatus according to the first embodiment shown in FIG. 1, a fluid of a mixture (heterogeneous system) (multi-phase system) including a gas, a liquid, or a liquid crystal is used as a "third fluid", and the third fluid may be introduced into the emulsifier 3, so that the fluid (a gas, a liquid, or a liquid crystal) in the heterogeneous system can be simultaneously enclosed in the same particles. The substances contained in the respective phases included in the first fluid 8 may be enclosed in the particles.

Second Embodiment

A second embodiment is an apparatus and method for producing a bilayer molecular membrane, a multilayer molecular membrane, a reversed bilayer molecular membrane, and a reversed multilayer molecular membrane.

Basic Structure of Apparatus For Producing Molecular Membrane

The basic structure of an apparatus for producing a molecular membrane is same as that of the apparatus for producing particles. That is, reference numeral 10 in FIGS. 9 and 10 denotes a molecular membrane. Accordingly, the molecular membrane can be produced by the apparatus for producing particles shown in FIGS. 1 to 5. For convenience of explanation, the apparatus for producing a molecular membrane is illustrated in FIG. 12.

Figure 12:
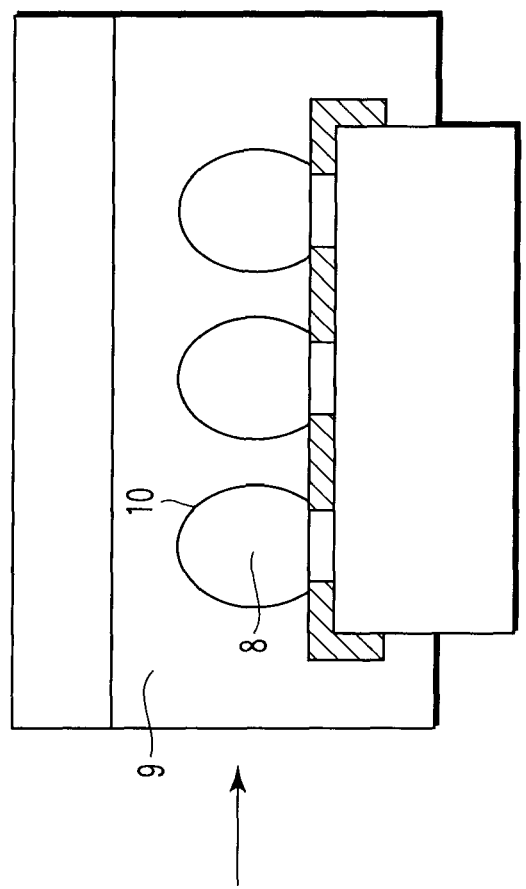
FIG. 12 shows an apparatus for producing a molecular membrane according to a second embodiment.
Figure 12:
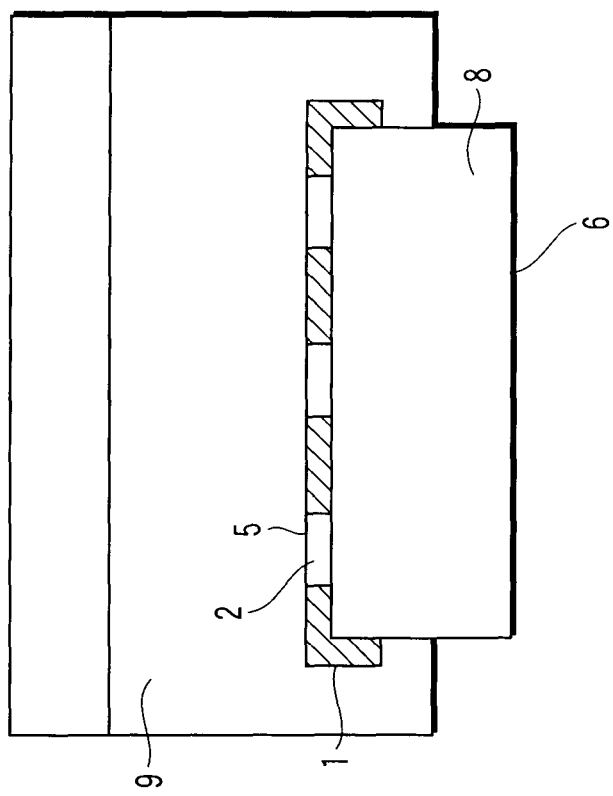

The apparatus for producing a molecular membrane shown in FIG. 12 comprises a fluid supplying member 6 to store a first fluid 8, a plunger unit 7 (not shown) for extruding the first fluid 8 from the fluid supplying member 6, and an emulsifier holding member 1 having through-holes 2 through which the first fluid 8 extruded from the fluid supplying member 6 passes. The emulsifier holding member 1 is attachable to and detachable from the fluid supplying member 6. The emulsifier holding member 1 is installed in a fluid supply port of the fluid supplying member 6 by a fitting or pinching manner. In addition, the emulsifier holding member 12 has at least two or more through-holes 2. Since the emulsifier holding member 1 has a plurality of through-holes 2, a large number of molecular membranes can be produced by one time operation of the plunger unit 7 (not shown). Further, an emulsifier is held in the through-holes 2. These points are same as those of the apparatus for producing particles.

With respect to the types and methods of use of the emulsifier, substances to be contained in the emulsifier, the first fluid and the second fluid for producing the molecular membrane are the same as those of the apparatus for producing particles, and explanation of them will be omitted herein.

Method For Producing Molecular Membrane

In the apparatus for producing a molecular membrane shown in FIG. 12, a method for producing a molecular membrane of an embodiment involves a step of holding the emulsifier 3 in the insides of the through-holes 2 through which the fluid extruded from the fluid supplying member 6 passes; a step of storing the first fluid 8 in the fluid supplying member 6; and a step of forming a molecular membrane 10 at the tip end parts of the through-holes 2 by extruding the first fluid 8 stored in the fluid supplying member 6 to the through-holes 2 holding the emulsifier 3. In the case where the emulsifier holding member 1 is attachable and detachable, the emulsifier is packed in the through-holes 2, the emulsifier holding member 1 is attached to the fluid supplying member 6, and thereafter, the first fluid 8 is supplied to the fluid supplying member 6. Herein, when a pressure is applied to the first fluid 8 by operation of the plunger unit 7 (not shown), the first fluid 8 is pushed out toward the lead-out ports 5 of the through-holes together with the emulsifier 3 held in the insides of the through-holes 2 of the emulsifier holding member 1. The emulsifier remains for a while at the positions while attaching to the lead-out ports 5 due to the affinity. At that time, a semispherical molecular membrane 10 is formed between the first fluid 8 pushed out of the through-holes 2 and the second fluid 9 in the outside of the system. The molecular membrane 10 has a semispherical form larger than the inner diameter of the lead-out ports 5.

The molecular membrane is to be obtained in the process of producing the particles 20. The production method is basically same as the method for producing particles, and therefore, detailed description of the production method will be omitted. However, in the case of producing the particles 20, the first fluid 8 is completely enclosed in the emulsifier 3, whereas in the case of producing the molecular membrane 10, the first fluid 8 is not enclosed in the emulsifier 3.

For example, in the case of producing a molecular membrane by using a system of an oleophilic lipophilic (Os), a first fluid 8 ($W_1$) which is a water phase, and a second fluid 9 ($W_2$) which is a water phase as shown in FIG. 9, the hydrophilic groups of the emulsifier are set toward the first fluid 8 and the second fluid 9 to form a bilayer or multilayer molecular membrane. The thickness and the shape of the molecular membrane 10 can be controlled by controlling the quantity of the emulsifier 3 held in the through-holes, the intensity of the affinity of the emulsifier 3 and the lead-out ports 5, and the injection amount of the first fluid 8. A molecular membrane having a steric structure (three-dimensional structure) can be produced by the invention. For example, the invention is suitable for producing a semispherical bimolecular membrane as shown in FIG. 9. Further, in the case where no solvent for dissolving the emulsifier 3 is used and the amount of the emulsifier 3 is sufficient, the hydrophilic groups of the emulsifier are set toward the first fluid 8 and the second fluid 9. Then, the emulsifier 3 may be further arranged orderly in several layers in the inside to produce a multilayer molecular membrane (refer to FIG. 8. FIG. 8 shows multilamellar particles).

On the other hand, in the case where other substances are added to the emulsifier 3, other substances may exist while being taken in the molecular assembly of the emulsifier which forms the molecular membrane 10. Additionally, an existence state of other substances contained in the emulsifier 3 is basically same as that in form of the above-mentioned particles, and detailed description thereof will be omitted.

Further, in the case where the molecular membrane 10 is produced by using a system of a hydrophilic emulsifier (Ws), a first fluid 8 ($O_1$) which is an oil phase, and a second fluid 9 ($O_2$) which is an oil phase as shown in FIG. 10, the hydrophobic groups of the emulsifier are set toward the first fluid 8 and the second fluid 9 to form a bilayer or multilayer molecular membrane 10 (reverse bilayer molecular membrane or reverse multilayer molecular membrane). The thickness and the shape of the molecular membrane 10 can be controlled by controlling the quantity of the emulsifier 3 held in the through-holes, the intensity of the affinity of the emulsifier 3 and the lead-out ports 5, and the injection amount of the first fluid 8. A molecular membrane having a steric structure (three-dimensional structure) can be produced by using the system shown in FIG. 10 similarly to the system shown in FIG. 9.

EXAMPLES

Hereinafter, practical examples of the first and second embodiments will be described further in detail.

Example 1

Sorbitan monooleate was used as the emulsifier 3, air was used as the first fluid 8, and pure water was used as the second fluid 9.

Sorbitan monooleate was applied to one face of a membrane-like nonwoven fabric (average pore size: 70 μm) made of nylon, which was an emulsifier holding member 1. After the nylon nonwoven fabric coated with sorbitan monooleate was fixed at the tip end of a syringe for injection serving as a fluid supplying member 6 with a rubber ring, the nonwoven fabric was immersed in pure water, and the air in the inside of the syringe was pushed out by the plunger unit 7. As a result, molecular membranes of sorbitan monooleate and bubbles were formed.

The bubbles produced by using the emulsifier and sorbitan monooleate were left as it was in the pure water for 3 hours to observe the stability of the bubbles. As a result, in the group of the bubbles, change of the particle size due to the flocculation or the coalescence of the bubble was not observed, or breakage of the bubbles was not observed during the observation. As a result of the above-mentioned observation, it can be confirmed that the bubbles of the invention can extremely stably exist.

Since the bubbles produced in this Example were produced using only sorbitan monooleate as the emulsifier, no lipophilic solvent other than sorbitan monooleate was contained in the oil phase (O) of V/O/W. Accordingly, in the oil phase (O), only the sorbitan monooleate molecules are arranged in a manner that the hydrophobic groups were set toward the air phase, which was the first fluid, and the hydrophilic groups were set toward the water, which was the second fluid. Consequently, bubbles having a thermodynamically stable vesicle structure could be produced.

Further, in the case of using a monoolein as the emulsifier in the above-mentioned production method, bubbles exhibiting little inconsistency in particle size could be produced in the same manner.

Example 2

Sorbitan monooleate was used as the emulsifier 3, air was used as the first fluid 8, and pure water was used as the second fluid 9. A silicon tube (thickness about 1000 μm) was used as the emulsifier holding member 1.

Fine holes were formed in the silicon tube by using a needle of a microsyringe. Sorbitan monooleate (the emulsifier 3) alone was applied to the outside of the tube, and one side of the tube was pinched with a clip to form an emulsifier holding member 1. As the configuration illustrated in FIG. 2, the other side of the silicon tube was connected to a lead-out port 15 (the lead-out ports 15 of the fluid supplying member 6) of the syringe. The lead-out ports 5 of the silicon tube was immersed horizontally in pure water serving as a second fluid 9, and the silicon tube side pinched with the clip was pulled to successively pushed out the sorbitan monooleate and air through the lead-out port 5. Accordingly, molecular membranes 10 of the sorbitan monooleate or bubbles of sorbitan monooleate (particles 20) exhibiting little inconsistency in particle diameter could be produced from the position where the holes were formed in the silicon tube.

This Example proved that the molecular membranes 10 or particles 20 could be produced by using the basic structure illustrated in FIG. 3. Further, in the case of using a deformable member for the emulsifier holding member, the through-holes were previously widened, and molecular membranes 10 or bubbles 20 exhibiting little inconsistency in particle diameter could be produced.

Example 3

Sorbitan monooleate was used as the emulsifier 3, air was used as the first fluid 8, and pure water was used as the second fluid 9.

Sorbitan monooleate was held previously in a film-like member 4 made of polypropylene having a large number of through-holes (through-hole diameter =100 μm and thickness =10 μm) to form emulsifier holding member 1 by the production method shown in FIG. 1. After the emulsifier holding member 1 holding the sorbitan monooleate was attached to the lead-out port 15 of a syringe (the lead-out port 15 of the fluid supplying member 6) as shown in FIG. 1, the emulsifier holding member 1 was immersed in pure water, and sorbitan monooleate and air were successively pushed out by the plunger unit 7 through the lead-out port 5. Accordingly, molecular membranes 10 of sorbitan monooleate or bubbles of sorbitan monooleate exhibiting little inconsistency in particle diameter could be produced.

Further, in the case of using the emulsifier holding member 1 having through-holes of the film-like member 4 made of polypropylene having a large number of through-holes in which segments of sorbitan monooleate and air were reciprocally held, molecular membranes 10 or particles 20 exhibiting little inconsistency in particle diameter could be produced.

In this connection, the thickness of the film-like member 4 having a large number of through-holes may be properly selected depending on the intensity and area of the membrane. Further, the particles 20 could be produced by the above-mentioned method even if Teflon (registered trademark), Naflon, silicon, nylon, vinyl, or fluoroglass (fluororesin [PTFE]-doped glass cloth) was used for the material of the film-like member 4.

Example 4

A light blue ink was used as the first fluid 8, and monoolein was used as the emulsifier 3. A Teflon (registered trademark) film having three through-holes (through-hole diameter =100 μm; and thickness =10 μm) was used as the emulsifier holding member 1. Other production conditions were same as those of Example 3.

Molecular membranes 10 obtained due to the blue ink being injected to the films made of monoolein were produced by successively leading out the monoolein (3) and the blue ink (8) through the lead-out port 5 into pure water (9). Next, when the blue ink (8) was further led out, the molecular membranes 10 were expanded to produce single inner aqueous phase type (inclosing blue ink) multilamellar monoolein vesicles (single inner aqueous phase type multilamellar vesicles) (20) in completely separated state from the lead-out port 5. When the multilamellar monoolein vesicles enclosing the blue ink were forcibly broken by outside force, the blue ink enclosed in the multilamellar monoolein vesicles was at once released.

After the liquid blue ink as the first fluid 8 was supplied to the fluid supplying member 6, air or oxygen in vapor phase as a third fluid 11 was led to prevent flow out of the blue ink to the first fluid 8 after production of the particles 20. In the case the quantity of the blue ink is small, air 11 may be enclosed together with the blue ink 8 in the same particles 20.

Example 5

Sorbitan monooleate was used as the emulsifier 3. Other production conditions were same as those of Example 4.

In this case, similarly to the case of using monoolein of Example 4, the molecular membranes 10 of sorbitan monooleate and the single inner aqueous phase type (blue ink inclusion) multilamellar sorbitan monooleate particles 20 (single inner aqueous phase type vesicles 20) were produced.

Example 6

Lecithin as a lipid was used as the emulsifier 3. A Naflon sheet (through-hole diameter =100 μm and thickness =1.0 mm) was used as the film-like member 4. Further, pure water heated to 50° C. by a hot plate was used as the second fluid 9. Other production conditions were same as those of Example 4.

In this case, similarly to the case of using monoolein of Example 4, the molecular membranes 10 of lecithin and multilamellar lecithin vesicles 20 (single inner aqueous phase type multilamellar vesicles 20) in which the blue ink was enclosed were produced.

Example 7

A light blue ink was used as the first fluid 8, and an emulsifier mixture 3 of sorbitan monooleate and lecithin having different HLB values (mixing weight ratio=3.9:1) as used as the emulsifier 3. The emulsifier mixture was prepared by mixing sorbitan monooleate (1.7 g) and lecithin (0.30 g) weighed by a microbalance with ultrasonic application. After the emulsifier mixture was kept still for a while after the mixing, the foams remaining in a small amount in the liquid surface were removed by using a dropping pipette. The amorphous precipitate emulsifiers were used as the other substances. Other production conditions were same as those of Example 6.

When the blue ink was injected to the emulsifier mixture, the molecular membranes 10 of sorbitan monooleate-lecithin were formed at the lead-out port 5. Further, in the state that the molecular membranes were produced, amorphous particles (other substances) were injected continuously together with the blue ink into the molecular membranes. Then, multilamellar vesicles 20 containing the sorbitan monooleate-lecithin emulsifier mixture enclosing the substance and blue ink, vesicles having little inconsistency in particle diameter (single inner aqueous phase type multilamellar vesicles enclosing the substance by the different emulsifier mixture) were produced.

This Example proved that even in the case of using the emulsifier mixture 3 prepared by using emulsifiers having different HLB values, single inner aqueous phase type multilamellar vesicles 20 could be produced. The Examples also proved that single inner aqueous phase type multilamellar vesicles 20 enclosing the substance could be produced.

It is not intended that the invention be limited to the illustrated embodiments. Modifications and substitutions to specific process conditions and structures can be made without departing from the spirit and scope of the invention.

What is claimed is:

1. An apparatus for producing molecular membranes or particles, comprising:
    a) a fluid-supplying member configured to store a first fluid;
    b) a plunger unit configured to extrude the first fluid from the fluid-supplying member; and
    c) an emulsifier-holding member having two or more through-holes to allow the first fluid extruded from the fluid-supplying member to pass therethrough, and holding an emulsifier in the through-holes such that the emulsifier blocks the through-holes,
    wherein a layer of emulsifier and a layer of the first fluid are alternately arranged in each of the through-holes.

2. An apparatus according to claim 1, wherein the emulsifier-holding member is attachable to and detachable from the fluid-supplying member.

3. The apparatus according to claim 1, wherein the emulsifier contains a solvent.

4. An apparatus for producing molecular membranes or particles, comprising:
    a) a fluid-supplying member configured to store a first fluid;
    b) a plunger unit configured to extrude the first fluid from the fluid-supplying member; and
    c) an emulsifier-holding member having two or more through-holes to allow the first fluid extruded from the fluid-supplying member to pass therethrough, and holding an emulsifier in the through-holes such that the emulsifier blocks the through-holes,
    wherein the emulsifier-holding member includes first and second members, the first member having first through-holes to allow the first fluid extruded from the fluid-supply member to pass therethrough and holding the emulsifier in the first through-holes such that the emulsifier blocks the first through-holes, the second member having second through-holes to allow a fluid and a particle produced at the first member to be extruded after making the particle and unblocking the emulsifier at the second member, and holding the emulsifier in the second through-holes such that the emulsifier blocks the second through-holes, diameters of the second through-holes being smaller than diameters of the first through-holes.

5. The apparatus according to claim 4, wherein the emulsifier-holding member further includes a second fluid between the first and second members.

6. The apparatus according to claim 4, wherein the second member is attachable to and detachable from the first member.

* * * * *